US00PP21870P2

(12) United States Plant Patent
Korlipara

(10) Patent No.: US PP21,870 P2
(45) Date of Patent: Apr. 12, 2011

(54) *ECHINACEA* PLANT NAMED 'LITTLE ANGEL'

(50) Latin Name: *Echinacea purpurea*
Varietal Denomination: Little Angel

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 12/653,629

(22) Filed: Dec. 14, 2009

(51) Int. Cl.
*A01H 5/00* (2006.01)

(52) U.S. Cl. ..... Plt./428

(58) Field of Classification Search ..... Plt./428
See application file for complete search history.

*Primary Examiner* — Kent L Bell

(74) *Attorney, Agent, or Firm* — Klarquist Sparkman, LLP

(57) ABSTRACT

A new and distinct *Echinacea* plant named 'Little Angel' characterized by numerous white, medium-small inflorescences, a well branched, compact, dwarf habit, and excellent vigor.

1 Drawing Sheet

Botanical denomination: *Echinacea purpurea.*

Variety designation: 'Little Angel'.

The present invention relates to a new and distinct cultivar of *Echinacea purpurea* and given the cultivar name 'Little Angel'. *Echinacea* is in the family Asteraceae. This new cultivar originated from a planned breeding project for a dwarf white flowering plant using proprietary, unnamed *Echinacea.* The closest comparisons on the market are *Echinacea* 'Pow Wow White' or 'White Swan', both unpatented plants. Compared to these cultivars, the new cultivar is much more compact.

This new *Echinacea purpurea* cultivar is distinguished by:

1. numerous white, medium-small flowers,
2. well branched, compact, dwarf habit,
3. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of a two year old *Echinacea purpurea* 'Little Angel' growing in the ground in the trial field in the summer in Canby, Oreg.

The following is a detailed description of the new *Echinacea* cultivar based on observations of 18-month old specimens growing in the ground in the field in full sun in the trial bed under typical outdoor conditions in Canby, Oreg. The plants had been moved from one trial field to another the fall before. Canby is in Zone 8 on the USDA Hardiness map Temperatures range from a high of 95 degrees F. in August to an average of 32 degrees F. in January. Normal rainfall in Canby is 42.8 inches per year in the trial fields in Canby, Oreg.

The color descriptions are all based on The Royal Horticultural Society Colour Chart, fifth edition.

Plant:

*Type.*—Herbaceous perennial.
*Hardiness.*—USDA Zones 4 to 9.
*Size.*—Grows from 28 to 33 cm wide and 29 to 31 cm tall to top of inflorescences.
*Form.*—Basal clump.
*Vigor.*—Excellent.
*Roots.*—Roots develop easily from cuttings from the crown.

Stem (flowering):

*Type.*—Ascending.
*Size.*—Branching up to3 times to 15 cm tall (to the upper most leaves) and 6 mm wide at base.
*Number of stems from the crown.*—15 to 20.
*Internode length.*—1.2 to 4 cm.
*Surface texture.*—Strigose.
*Color.*—Yellow Green 146A.

Leaf (basal):

*Type.*—Simple.
*Shape.*—Ovate to lanceolate.
*Arrangement.*—Basal.
*Blade size.*—Grows to 15 cm long and 5.2 cm wide.
*Margins.*—Coarsely serrate.
*Apex.*—Acute.
*Base.*—Attenuate.
*Surface texture.*—Strigose on both sides.
*Venation.*—Pinnate.
*Color.*—Topside, Green 137A with the vein Yellow Green 144C and bottom side closest to Yellow Green 147B with the vein Yellow Green 149D.
*Petiole description.*—Grows to 12 cm long and 5 mm wide, somewhat strigose, Yellow Green 146C.

Leaf (stem):

*Type.*—Simple.
*Shape.*—Ovate to lanceolate.
*Arrangement.*—Alternate.
*Blade size.*—Grows to 8.2 cm long and 3.2 cm wide.
*Margins.*—Coarsely serrate.
*Apex.*—Acute to acuminate.
*Base.*—Attenuate, continuing down petiole, clasping.

*Surface texture.*—Strigose on both sides.

*Venation.*—Pinnate.

*Color.*—Topside, Green 137A with the vein Yellow Green 144C and bottom side closest to Yellow Green 147B with the vein Yellow Green 149D.

*Petiole description.*—Grows to 3 cm long on lower leaves and 3 mm wide, strigose, Yellow Green 145C.

Inflorescence:

*Type.*—composite on terminal stalked heads.

*Number of flowering stems per plant in summer.*—15 to 20 from the crown, some branching.

*Flowering stem.*—Grows to 24.5 cm tall from the base of the plant to the terminal inflorescence and can grow to 10.5 cm long from the top leaf to the base of an inflorescence; branched, 1 to 4 inflorescences per stem; diameter growing to 1 cm wide near the inflorescence; strigose, Yellow Green 146A.

*Size of inflorescence.*—Grows to 10 cm wide and 2 cm deep as disc enlarges.

*Form.*—Ray florets held mostly perpendicular to the stem, then dropping down slightly; mature disc is conic.

*Immature inflorescence.*—3.5 cm wide and 2.2 cm deep, ray florets held at a 45 degree angle and rolled up so only the back color shows, Green Yellow 1D.

*Ray florets.*—Without pistil or stamen, 13 to 19 in number, oblanceolate with the tip cupped and 2 toothed (each acute), entire margins, base attenuate, grows to 3.7 cm long and 11 mm wide, glabrous on both sides; sometimes with 1-2 upward projections from base, to 17 mm long and 3 mm wide; topside White 155A, bottom side White 155A with Yellow Green 144A at base and tints of Green Yellow 1D on main veins

*Disc.*—Slightly convex becoming conic, becoming 2 cm deep and 3 cm wide with maturity, color Yellow Orange 22A on bracts, and Yellow Green 147B as the base color.

*Disc florets.*—About 250 in number, with pistil and stamen, tubular in shape, 9 mm long and 1.1 mm wide, each with one persistent, very stiff bract (12 mm long and Orange 22A on the top ⅓, Yellow Green 146C on middle ⅓, White NN155A on bottom ⅓); corolla 5 mm long and 1.1 mm wide, 5 lobed, lobes acute, margins entire, glabrous, Yellow Green 146D, pistil 9 mm long, ovary 3 mm long, White 155C, style 5 mm long, Yellow Green 145B, with an extruding, 2-branched stigma spreading 2 mm wide, Yellow Green 145B; stamen 4 in number, 4 mm long, anthers 2.5 mm long and Brown 200A, filaments 1.5 mm long, White 155C, pollen not seen.

*Phyllaries.*—In 3 leafy series, area 25 mm wide and 8 mm long, lobes lanceolate in shape, reflexed, grow to 6 mm long and 3 mm wide, surface strigose, tip acute, margin entire, Yellow Green 147A on both sides.

*Receptacle.*—Grows to 10 mm wide and 12 mm deep, White 155B.

*Bloom period.*—July through October in Canby, Oreg.

*Fragrance.*—Nice, floral.

*Lastingness.*—Each inflorescence lasts about two weeks in Canby, Oreg.

Seeds: none seen.

*Fertility.*—Low.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

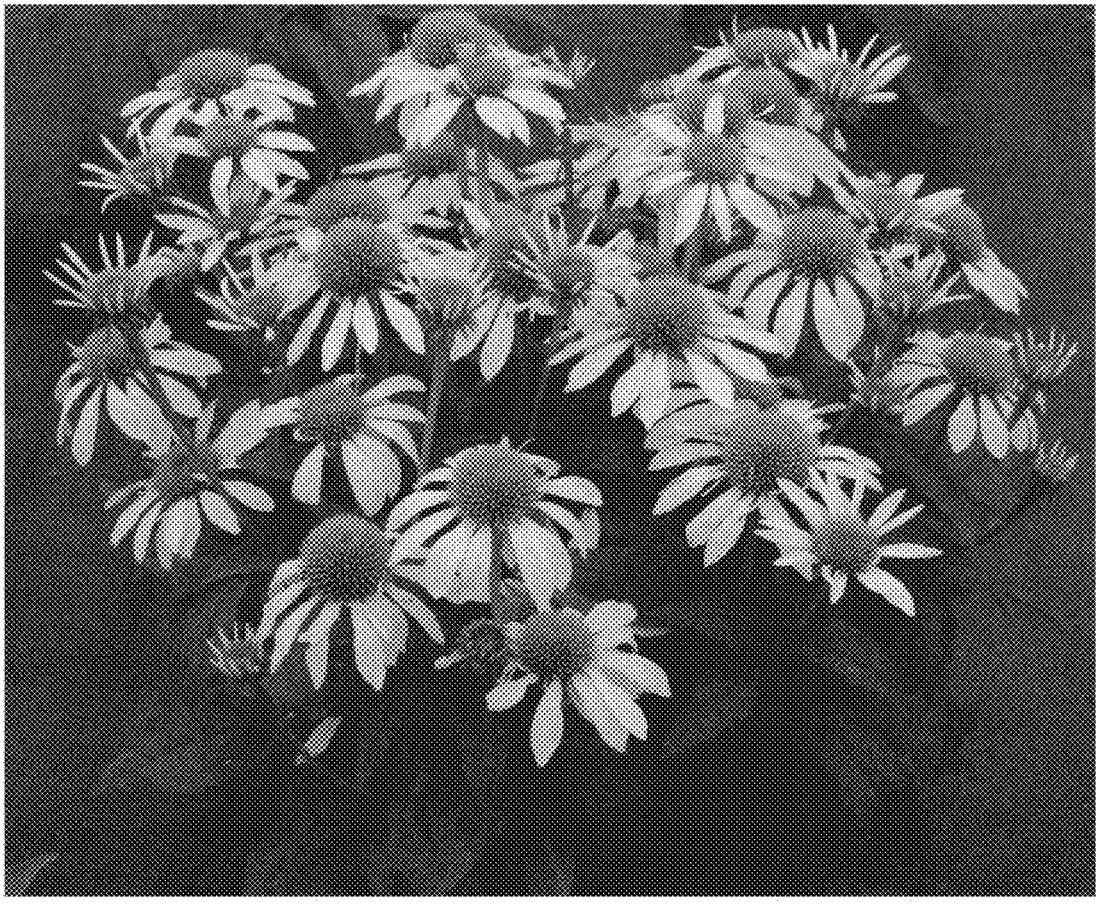

* * * * *